United States Patent [19]

Fecondini

[11] Patent Number: 4,861,485

[45] Date of Patent: Aug. 29, 1989

[54] HEMODIAFILTRATION DEVICE

[75] Inventor: Luciano Fecondini, Bologna, Italy

[73] Assignee: W. R. Grace & Co., Lexington, Mass.

[21] Appl. No.: 174,068

[22] Filed: Mar. 28, 1988

[30] Foreign Application Priority Data

Jan. 22, 1988 [IT] Italy .................. 19179 A/88

[51] Int. Cl.[4] .......................................... B01D 13/01
[52] U.S. Cl. ........................... 210/641; 210/314;
210/321.64; 210/321.8; 210/321.89; 210/646;
210/806; 604/5
[58] Field of Search .............. 210/259, 314, 315, 317,
210/321.64, 321.72, 321.78, 321.79, 321.8, 641,
645, 646, 806, 195.2, 321.89, 321.81, 500.23;
604/4, 5, 6

[56] References Cited

U.S. PATENT DOCUMENTS

| | | | |
|---|---|---|---|
| Re. 32,186 | 6/1986 | Bentley | 210/646 |
| 3,619,423 | 11/1971 | Galletti et al. | 210/641 |
| 3,727,612 | 4/1973 | Sayers et al. | 210/641 |
| 4,000,072 | 12/1976 | Sato et al. | 210/321.8 |
| 4,094,775 | 6/1978 | Mueller | 210/646 |
| 4,303,068 | 12/1981 | Zelman | 604/5 |
| 4,312,757 | 1/1982 | Brumfield | 210/646 |
| 4,498,990 | 2/1985 | Shaldon et al. | 210/321.8 |
| 4,581,141 | 4/1986 | Ash | 210/502 |

OTHER PUBLICATIONS

B. von Albertini et al., High-Flux Hemodiafiltration: Under Six Hours/Week Treatment, 1984, vol. 30, Trans Am Soc. Artif. Internal Organs, pp. 227–231.
J. H. Miller et al., Technical Aspects of High-Flux Hemodiafiltration for Adequate Short (Under 2 Hours) Treatment, 1984, vol. 30, Trans. Am. Soc. Artif. Organs, pp. 377–381.
B. von Albertini et al., Performance Characteristics of High-Flux Haemodiafiltration, Proc. EDTA-ERA (1984), vol. 21, pp. 447–453.
B. von Albertini et al., High Flux Hemodiafiltration, 1984, The Am. Soc. of Nephrology, vol. 27, p. 174, (Pub. 1985).

Primary Examiner—W. Gary Jones
Attorney, Agent, or Firm—Stacey L. Channing; William L. Baker

[57] ABSTRACT

Disclosed herein is a hemodiafiltration cartridge and apparatus and methods utilizing said cartridge. Said cartridge comprises: a dialysate inlet; a dialysate outlet; a blood inlet; a blood outlet; a first semipermeable membrane means for sterilizing and depyrogenating dialysate prior to its contact with blood; and a second semipermeable membrane means for the removal of wastes from blood.

42 Claims, 3 Drawing Sheets

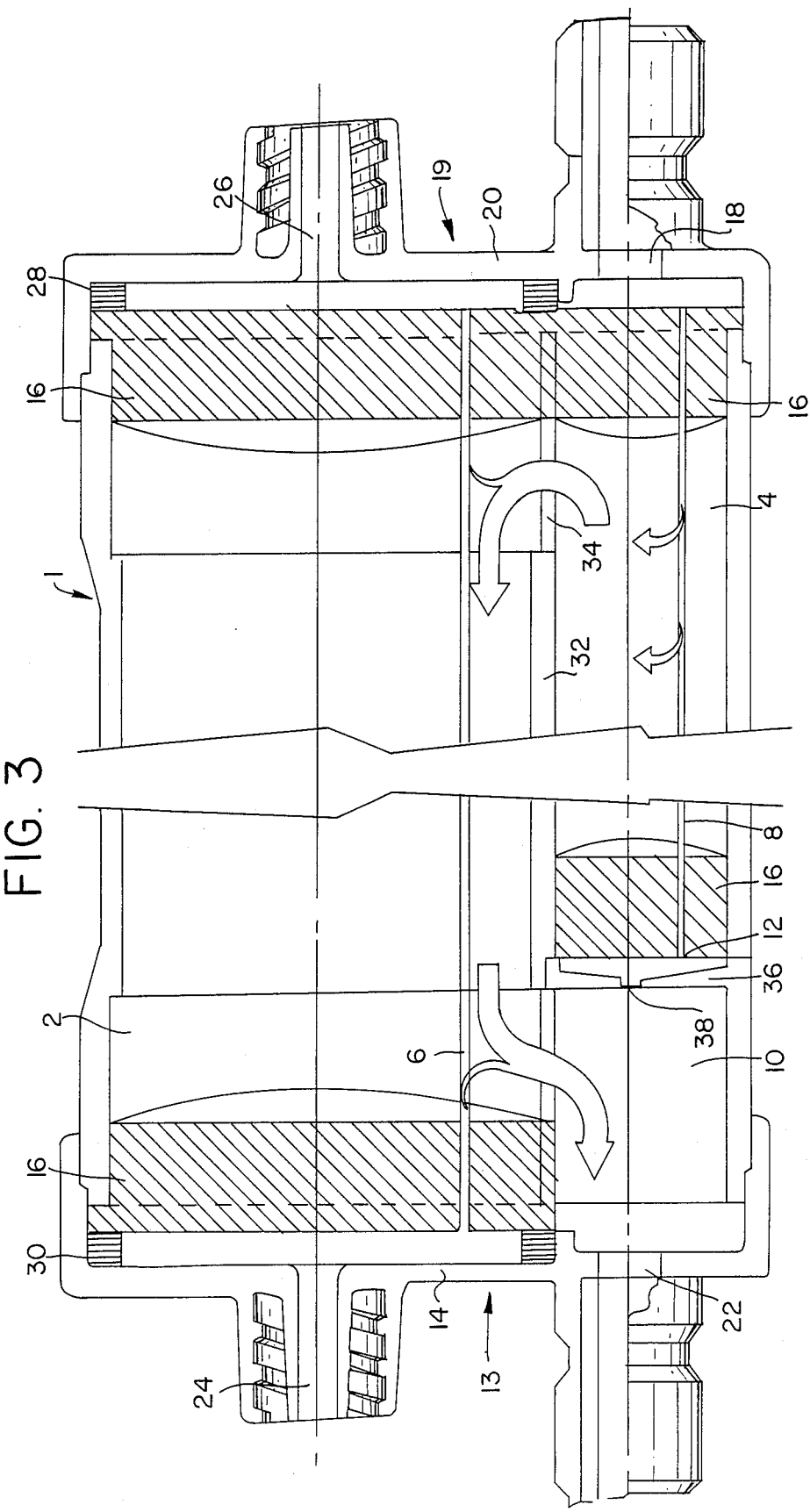

HEMODIAFILTRATION DEVICE

BACKGROUND OF THE INVENTION

This invention relates to hemodiafiltration cartridges, hemodiafiltration apparatus and hemodiafiltration methods.

When the kidneys in mammals fail to remove metabolic waste products from the body, most of the other body organs soon fail also. The symptoms which develop are termed uremia and the severity of these symptoms is proportional to the retention in the blood of metabolic waste products ordinarily excreted by the kidneys, two of the most toxic waste products being urea and creatinine. Various other metabolic products which can accumulate in the bloodstream include polypeptides, phenols, amines, guanidine, and a variety of middle molecules in the molecular weight range of 500–3000 daltons. The kidneys also provide electrolyte balance in the body when functioning normally, excreting $Na^+$, $K^+$, $H^+$, $Mg^{++}$, $Ca^{++}$, $Cl^-$, $HCO_3^-$, $PO_4^{-3}$, etc. ions in excess of body needs. When kidney failure occurs, the metabolic waste products will not be excreted and the proper electrolyte balance will not be maintained.

Hemodialysis (dialysis of the blood outside of the body) removes solutes, such as creatinine and urea, from the blood by diffusion down a concentration gradient. The solutes diffuse across a semipermeable membrane into a second liquid. Ultrafiltration removes small and middle size solutes by convective mass transfer. Basically, hydrostatic pressure causes solutes as well as plasma water to pass through the wall of a semipermeable membrane. Hemodiafiltration utilizes both diffusive and convective mass transfer and thus is a combination of hemodialysis and ultrafiltration.

Plasma water lost from the blood during hemodiafiltration or ultrafiltration needs to be replaced, at least in part. This replacement of fluid with sterile, non-pyrogenic fluid is currently accomplished in many ways such as by: (1) intravenous infusion; (2) adding sterile fluid in line before or after the filter cartridge and before the patient's body; and (3) backfiltration of dialysate which has been sterilized by the use of filter equipment connected to the filter cartridge. These current fluid replacement methods have many drawbacks. Intravenous infusion or replacement of fluid loss in line before or after the filter cartridge require the use of expensive sterile materials. Connecting filter equipment to the filter cartridge requires the use of bulky filter equipment and problems have occurred with providing a sterile and non-pyrogenic dialysate transfer.

Accordingly, the principal object of this invention is to provide a hemodiafiltration apparatus which has the capability of replacing lost fluid in the patient with sterile and non-pyrogenic dialysate without the use of additional filter equipment for dialysate treatment and without the use of expensive sterile materials.

It is a further object of the invention to provide a hemodiafiltration cartridge for said hemodiafiltration apparatus that has traditional connectors for blood and dialysate and thus can be used with standard dialysis apparatus.

It is still a further object of the invention to provide such a hemodiafiltration apparatus which is quite efficient in terms of time and expense.

SUMMARY OF THE INVENTION

The problems of the prior art are solved by the provision of the hemodiafiltration cartridge of the invention which comprises: a dialysate inlet; a dialysate outlet; a blood inlet; a blood outlet; a first semipermeable membrane means for sterilizing and depyrogenating dialysate prior to its contact with blood; and a second semipermeable membrane means for the removal of wastes from blood. The cartridge is generally tubular and has two ends, a first end and a second end defined respectively by two end walls, a first end wall and a second end wall. The dialysate inlet and the blood outlet are preferably located at the first end of said cartridge and the dialysate outlet and the blood inlet are preferably located at the second end of the cartridge. Accordingly, said first end wall of the cartridge preferably has openings for the dialysate inlet and the blood outlet and said second end wall of the cartridge preferably has openings for the dialysate outlet and the blood inlet. Preferably, the first and second semipermeable membrane means each comprise a plurality (bundle) of semipermeable hollow fibers, the hollow fibers of each preferably being open at both ends. The bundle of hollow fibers of the second semipermeable membrane means extend generally longitudinally through said cartridge, from one end to the other, one end of said bundle of fibers being in communication with the blood inlet and the other end of said bundle of fibers being in communication with the blood outlet. The bundle of hollow fibers of the first semipermeable membrane means extend generally longitudinally in said cartridge from the first end of the cartridge towards the second end of said cartridge, one end of the bundle of fibers (the first bundle end) extending to the first end of the cartridge and being in communication with the dialysate inlet. Preferably, the hollow fibers of the first semipermeable membrane means do not reach the second end of the cartridge and the cartridge further comprises a plenum extending generally longitudinally from the other end of the bundle of fibers (the second bundle end) to the second end of the cartridge, said plenum being in communication with the dialysate outlet. Preferably, the plenum is bounded by a barrier means, such as a wall, which extends laterally between th second bundle end of the first semipermeable membrane means and said plenum and there is a tiny opening in said barrier means for the air, if any exists, in the hollow fibers of the first semipermeable means and for a very small quantity of the dialysate which has entered the hollow fibers of the first semipermeable membrane means to pass into the plenum and out of the cartridge via the dialysate outlet.

A method of the invention comprises the steps of: (a) providing a hemodiafiltration cartridge of the invention; (b) passing dialysate through the dialysate inlet into the hollow fibers of the first semipermeable membrane means; (c) passing dialysate from the hollow fibers of the first semipermeable membrane means through the walls of said hollow fibers, a portion of said dialysate entering into the hollow fibers of the second semipermeable membranes means through the walls of said hollow fibers of the second semipermeable membrane means and the remainder of the dialysate surrounding the exterior of the hollow fibers of the second semipermeable membrane means; (d) passing blood through the blood inlet and into said hollow fibers of the second semipermeable means; (e) passing blood wastes and blood plasma water through the walls of the hollow fibers of the second semipermeable membrane means into said dialysate surrounding the second semipermeable means; (e) passing the blood minus the blood wastes and blood plasma water in the hollow fibers of the second semipermeable membrane means together with the dialysate in the hollow fibers of the second semipermeable membrane means into the blood outlet; and (f) passing the dialysate surrounding the second semipermeable membrane means with the blood wastes and blood plasma water lost from the blood into the dialysate outlet. Preferably the method of the invention further comprises a step of passing a minimal amount of the dialysate which has entered into the hollow fibers of the first semipermeable membrane means and any air in the hollow fibers of the first semipermeable membrane means out of the cartridge via a tiny opening. In the preferred cartridge of the invention, said tiny opening is preferably located in the barrier means bounding the plenum.

BRIEF DESCRIPTION OF THE DRAWINGS

FIG. 3 is a schematic view of a cross-section of a cartridge of the invention which illustrates the method of functioning of the cartridge.

DESCRIPTION OF THE PREFERRED EMBODIMENT

Figure 1:
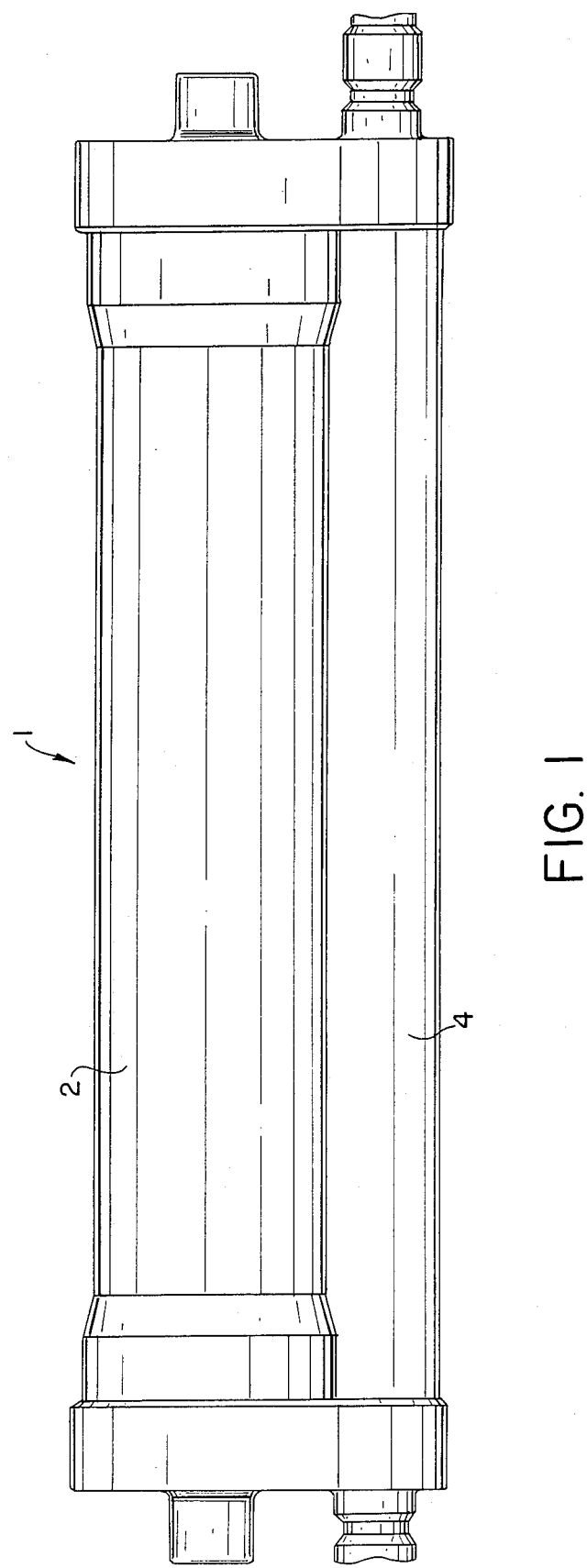
FIG. 1 is a side view of a cartridge of the invention.

The hemodiafiltration cartridge of the invention comprises a dialysate inlet; a dialysate outlet; a blood inlet; a blood outlet; a first semipermeable membrane means for sterilizing and depyrogenating dialysate prior to its contact with blood; and a second semipermeable membrane means for the removal of wastes from blood. The cartridge is preferably substantially tubular and has two ends, a first end and a second end defined respectively by two end walls, a first end wall and a second end wall. For the preferred counterflow mode of operation, the dialysate inlet and the blood outlet are located at or adjacent to the first end of the cartridge and the dialysate outlet and the blood inlet are located at or adjacent to the second end of the cartridge. Accordingly, the first end wall of the cartridge may have openings for the dialysate inlet and the blood outlet and the second end wall of the cartridge may have openings for the dialysate outlet and the blood inlet.

Although the first and second semipermeable membrane means may take any form, the first and second semipermeable membrane means preferably each comprise a plurality (bundle) of hollow fibers, hollow fibers offering the advantage of high surface area in a very compact volume. The first semipermeable membrane means and the second semipermeable membrane means can be made from the same or a different material. The first semipermeable membrane means can comprise any material standardly used for sterile and pyrogenic filtration of dialysate. Suitable materials for the first semipermeable membrane means include polysulfone, polyamide, polyacrylonitrite and cellulose based materials such as cellulose acetate. The first semipermeable membrane means preferably has a molecular weight pore size cutoff of at least 1000 daltons and more preferably has a molecular weight pore size cutoff that ranges from 1000 to 30,000 daltons. The second semipermeable membrane means can comprise any standard hemodiafiltration membrane. Suitable materials for the second semipermeable membrane include polysulfone, polyamide, polyacrylonitrite and cellulose acetate, with the preferred material being polysulfone. The second semipermeable membrane means preferably has a molecular weight pore size cutoff of no greater than 55,000 daltons so that albumin will not pass through said membrane. The second semipermeable membrane means more preferably has a molecular weight pore size cutoff that ranges from 30,000–50,000 daltons.

The second semipermeable membrane means preferably comprises a plurality of semipermeable hollow fibers, open at both ends, said plurality of hollow fibers extending generally longitudinally through the substantially tubular cartridge from the first end of the cartridge to the second end of the cartridge. The hollow fibers are preferably positioned relative to each other and secured within the cartridge by a standard potting compound. After the fibers are potted by techniques known in the art, the ends are cut so that the hollow fibers are open at both ends. In order for blood to be able to flow into and out of said hollow fibers, one end of the bundle of hollow fibers is in communication with the blood inlet and the other end is in communication with the blood outlet. The packing density of the hollow fibers of said second semipermeable membrane means is between about 30% and about 70% and preferably between about 40% and 60%.

In one embodiment of the cartridge of the invention, the first semipermeable membrane means preferably comprises a plurality of semipermeable hollow fibers, all of said fibers being open at the same end and closed at the opposite end, said plurality of semipermeable hollow fibers extending generally longitudinally in the substantially tubular cartridge from the first end of the cartridge towards the second end of the cartridge, the open ends of the hollow fibers extending to the first end of the cartridge and being in communication with the dialysate inlet in order for dialysate to be able to flow into said hollow fibers. Although it is possible for the semipermeable hollow fibers of the first semipermeable membrane means to extend longitudinally the entire distance from the first end of the cartridge to the second end of the cartridge, it is preferable that the hollow fibers do not reach the second end of the cartridge and that the cartridge further comprises a plenum extending generally longitudinally from the closed ends of the hollow fibers to the second end of the cartridge, said plenum being in communication with the dialysate outlet. The hollow fibers are preferably positioned relative to each other and secured within the cartridge by a standard potting compound. For purposes of potting (so that potting resin does not run into the plenum), the plenum is preferably bounded by a barrier means, such as a wall, which extends laterally between the closed ends of the hollow fibers and said plenum. After the fibers are potted by techniques known in the art, the ends of the fibers which extend to the first end of the cartridge are cut so that these ends are open. Said open ends are in communication with the dialysate inlet in order for the dialysate to be able to flow into said hollow fibers.

By having the hollow fibers of the first semipermeable membrane means closed at one end, the dialysate flowing into the dialysate inlet and entering the hollow fibers of the first semipermeable membrane means at the open end of the bundle of fibers is forced to pass through the walls of the hollow fibers. Since bacteria and most pyrogenic materials cannot pass through the walls of the hollow fibers, the dialysate which has passed through the walls of the hollow fibers is thus sterile and non-pyrogenic.

Because the hollow fibers of the first semipermeable means are closed at one end, it is possible that air will be trapped inside the hollow fibers, potentially compromising the filtration of dialysate. Although any means of preventing air from entering the hollow fibers of the first semipermeable membrane means, e.g., by some design modification in the hemodiafiltration apparatus, or of removing the air from the hollow fibers of the first semipermeable membrane means will do if the trapped air in said hollow fibers presents a significant problem, one way of removing the air from the hollow fibers is accomplished by the provision of a second embodiment of the cartridge of the invention described below.

In such a second embodiment, the first semipermeable membrane means comprises a plurality of semipermeable hollow fibers, open at both ends, said plurality (bundle) of hollow fibers extending generally longitudinally in the substantially tubular cartridge from the first end of the cartridge towards the second end of the cartridge, said bundle of fibers having two ends, a first bundle end and a second bundle end, one end of the bundle of fibers (the first bundle end) extending to the first end of the cartridge and being in communication with th dialysate inlet in order for dialysate to be able to flow into said hollow fibers. Although it is possible for the semipermeable hollow fibers of the first semipermeable membrane means to extend longitudinally the entire distance from the first end of the cartridge to the second end of the cartridge, it is preferable that the hollow fibers do not reach the second end of the cartridge and that the cartridge further comprises a plenum extending generally longitudinally from the other end of the bundle of fibers (the second bundle end) to the second end of the chartridge, said plenum being in communication with the dialysate outlet. The hollow fibers are preferably positioned relative to each other and secured within the cartidge by a standard potting compound. After the fibers are potted by techniques known in the art, the ends are cut so that the hollow fibers are open at both ends. In order for the dialysate to be able to flow into said hollow fibers, the first bundle end of said fibers is in communication with the dialysate inlet. Since it is desired to have a passageway from the second bundle end of the fibers to the outside of the cartridge so that air will not be trapped in said fibers, but it is necessary for the purpose of the invention that very little dialysate flow out of said hollow fibers of the first semipermeale membrane means to the outside of the cartridge, the second bundle end of said fibers is in communication with the outside of the cartridge via a tiny opening. Preferably, the plenum, discussed above, is bounded by a barrier means, such as a wall, which extends laterally between the second bundle end of the first semipermeable membrane means and said plenum, and the tiny opening is located in said barrier means. The tiny opening is designed in such a way as to guarantee minimal dialysate loss and complete removal of air that would otherwise compromise the filtration of dialysate. For example, the dialysate flowing through the tiny opening will preferably be kept to less than 10% and more preferably less than 5% of the dialysate entering the hollow fibers of the first semipermeable membrane means via the dialysate inlet, the remainder of the dialysate being forced to pass through the walls of said hollow fibers of the first semipermeable membrane means, thus sterilizing and depyrogenating said dialysate. The small amount of dialysate passing through the tiny opening will be pyrogen concentrated, but this presents no problem since said small amount of dialysate immediately exits the cartridge. In fact, there may be a beneficial aspect in that there is less pyrogen concentrated in the hollow fibers of the first semipermeable membrane means and thus there is less pyrogen that might be able to pass through the hollow fiber walls, i.e., pyrogenic materials with very low molecular weights.

In both the first and the second embodiments of the cartridge of the invention, the packing density of the hollow fibers of said first semipermeable membrane means is between about 30% and about 70% and preferably between about 40% and about 60%.

Figure 2:
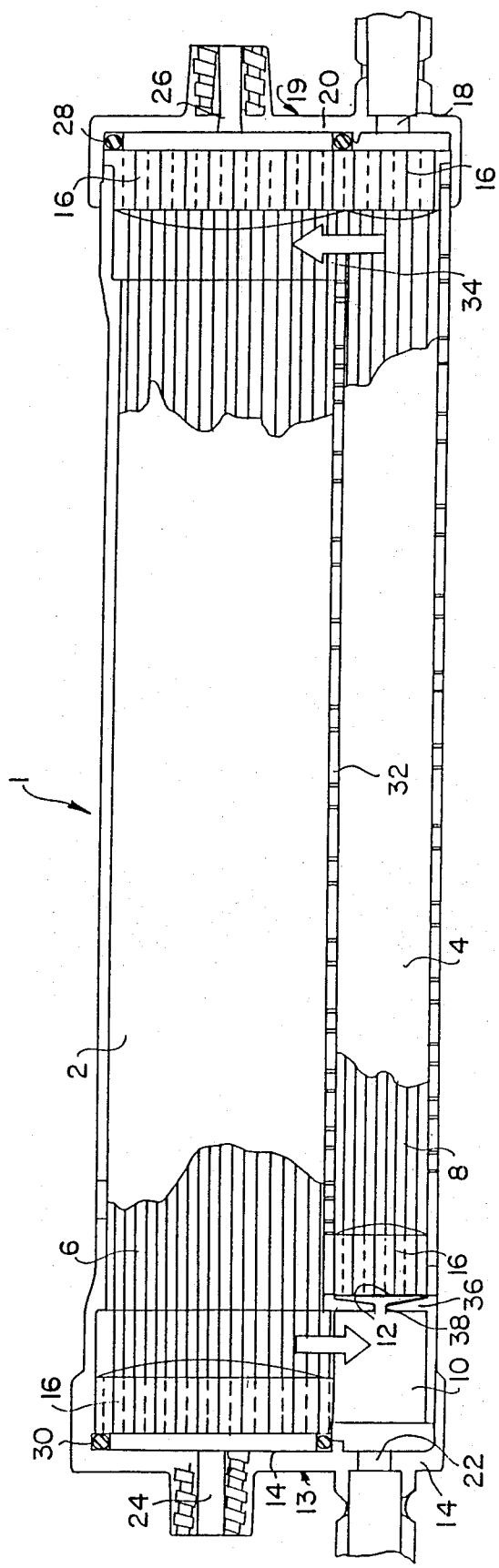
FIG. 2 is a side view of a cartridge of the invention which is cut away to show certain essential elements thereof in cross-section.

FIG. 1 illustrates a cartridge of the invention. FIGS. 2 and 3 illustrate the second embodiment of the cartridge of the invention. As seen in FIGS. 2 and 3, said cartridge 1 preferably has two generally cylindrical chambers, a blood chamber 2 and a dialysate chamber 4, the blood chamber 2 containing the second semipermeable membrane means 6 comprising a plurality of hollow fibers open at both ends and the dialysate chamber 4 containing the first semipermeable membrane means 8 comprising a plurality of hollow fibers open a both ends and the plenum 10 extending from the second bundle end 12 of the hollow fibers of the first semipermeable membrane means 8 to the second end 13 of the cartridge defined by the second end wall 14. (In the first embodiment of the cartridge of the invention, the ends of the hollow fibers at the second bundle end would be closed.) Said end wall 14 is preferably formed by a cap with two openings, one for the blood inlet and the other for the dialysate outlet. The first end 19 of the cartridge is defined by the first end wall 20, said end wall 20 preferably being formed by a cap with two openings, one for the blood outlet and one for the dialysate inlet. As above-described, the plurality of hollow fibers of the first and second semipermeable membrane means are relative to each other and secured within the cartridge by a standard potting compound 16. The dialysate inlet 18 is located on the portion of the first end wall 20 of the cartridge which bounds the dialysate chamber 4, the dialysate outlet 22 is located on the portion of the second end well 14 of the cartridge which bounds the dialysate chamber 4, the blood inlet 24 is located on the portion of the second end wall 14 of the cartridge which bounds the blood chamber 2 and the blood outlet 26 is located on the portion of the first end w 11 20 of the cartridge which bounds the blood chamber 2. The blood chamber 2 and the dialysate chamber 4 are separated from each other at the first end of the cartridge by a separating means, such as an O-ring 28, and at the second end of the cartridge by a separating means such as an O-ring 30.

As seen in FIGS. 2 and 3, the dialysate chamber 4 and the blood chamber 2 are preferably partially separated from each other in the interior of the cartridge by a barrier means 32, such as a wall, extending substantially longitudinally in the cartridge from the second bundle end 12 of the hollow fibers of the first semipermeable membrane means towards the first end of the cartridge, but not reaching the first end of the cartridge the space 34 from the barrier means 32 to the first end of the cartridge serving to allow dialysate to flow from the dialysate chamber 4 into the blood chamber 2. Because of the barrier means 32, the sterile and non-pyrogenic dialysate, which has passed through the walls of the hollow fibers in the dialysate chamber 4, can only pass into the blood chamber 2 at the space 34. Thus, the purified dialysate will flow in the blood chamber 2 from the first end of the cartridge to the second end of the cartridge while the blood entering the blood chamber 2 at the blood inlet 24 will flow from the second end of the cartridge to the first end of the cartridge. By having the blood and dialysate flow in this preferred countercurrent way, optimal clearance performance are guaranteed. The plenum 10 is preferably bounded by a barrier means 36, such as wall, which extends laterally between the second bundle end 12 of the hollow fibers and said plenum 10. The barrier means 36 further comprises a tiny opening 38 through which any existing air in the hollow fibers of the first semipermeable membrane means and a very small quantity of dialysate in said hollow fibers can pass into the plenum 10 and out of the cartridge via the dialysate outlet 22.

The hemodialfiltration cartridge of the invention has traditional connectors for blood and dialysate and thus can be used with standard dialysis apparatus. Hemodiafiltration apparatus which includes the hemodiafiltration cartridge of the invention will generally comprise a dialysate reservoir; conduit means, such as tubing, for connecting the dialysate reservoir to the dialysate inlet (preferably a Hansen dialysate port) of the cartridge; conveying means, such as a pump, for passing dialysate from the dialysate reservoir into the cartridge via the dialysate inlet and out of said cartridge via the dialysis outlet (preferably a Hansen dialysate port); conduit means, such as blood tubing, for connecting the bloodstream of a patient (e.g. an artery) to the blood inlet (preferably a Lock blood port of the cartridge; conduit means, such as blood tubing, for connecting the blood outlet (preferably a Lock blood port) of the cartridge to the bloodstream of the patient (e.g. a vein); and conveying means, such as a pump, for passing blood from an artery in the bloodstream into the cartridge via the conduit means connecting the bloodstream to the blood inlet and via the blood inlet and for passing treated blood out of the cartridge to a vein in the blood stream via the blood outlet and via the conduit means connecting the blood outlet to the bloodstream. Since the dialysate is preferably at the same temperature as the blood, the hemodiafiltration apparatus preferably includes some form of heating means for the dialysate. In addition, the hemodialfiltration apparatus preferably includes monitoring equipment for blood and dialysate pressure, for dialysate temperature and for concentration of electrolytes in the dialysate. The apparatus may also contain means to introduce anticoagulants such as hirudin or heparin into the blood to prevent clotting of the blood on all surfaces of the apparatus that are in contact with blood.

A hemodiafiltration method of the invention utilizing the hemodiafiltration device of the invention comprises the steps of: passing dialysate through the dialysate inlet into the hollow fibers of the first semipermeable membrane means; passing dialysate from the hollow fibers of the first semipermeable membrane means through the walls of the hollow fibers of the first semipermeable membrane means, a portion of the dialysate entering into the hollow fibers of the second semipermeable membrane means through the walls of said hollow fibers and the remainder of the dialysate surrounding the exterior of the hollow fibers of the second semipermeable membrane means; passing blood from an artery in the bloodstream of a patient through the blood inlet and into the hollow fibers of the second semipermeable membrane means; passing blood wastes and some blood plasma water through the walls of the hollow fibers of the second semipermeable membrane means into the dialysate surrounding the second semipermeable membrane means; passing the blood minus the blood wastes nd blood plasma water in the hollow fibers of the second semipermeable membrane means together with the dialysate in the hollow fibers of the second semipermeable membrane means into the blood outlet; and passing the dialysate surrounding the second semipermeable membrane means with the blood wastes and blood plasma water lost from the blood into the dialysate outlet. Preferably, the method of the invention further comprises a step of passing any air in the hollow fibers of the first semipermeable membrane means out of the cartridge.

In the method of the invention in which the cartridge depicted in FIGS. 2 and 3 is used, a minimal amount (less than 10% and preferably less than 5%) of the dialysate which has entered into the hollow fibers of the first semipermeable membrane means via the dialysate inlet and any air in the hollow fibers of the first semipermeable membrane means passes from the open ends of said hollow fibers at said second bundle end 12 into plenum 10 via opening 38 and out of the cartridge via dialysate outlet 22. The remainder of the dialysate which has entered into said hollow fibers via the dialysate inlet passes through the walls of the hollow fibers of the first semipermeable membrane means (schematically depicted in FIG. 3) and into the blood chamber 2 at the space 34 (also schematically depicted in FIG. 3), a portion of said dialysate in the blood chamber entering into the hollow fibers of the second semipermeable membrane means through the walls of said hollow fibers and the rest of said dialysate in the blood chamber surrounding the exterior of the hollow fibers of the second semipermeable membrane means. Since dialysate enters into the blood chamber at space 34, the purified dialysate will flow in the blood chamber 2 in a substantially opposite direction than the blood flowing through the blood chamber 2 in the hollow fibers of the second semipermeable membrane means, said countercurrent flow being quite preferred. Also, when the preferred cartridge of the invention depicted in FIGS. 2 and 3 is used, the dialysate surrounding the second semipermeable membrane means together with the blood wastes and blood plasma lost from the blood pass into the dialysate outlet through the plenum 10 (schematically depicted in FIG. 3).

Not only is the dialysate sterilized and depyrogenated within the cartridge by its forced passage from inside the hollow fibers of the first semipermeable membrane means through the walls of said hollow fibers, but the portion of dialysate that enters into the hollow fibers of the second semipermeable membrane means through the walls of said hollow fibers is further purified by said passage through the walls of the hollow fibers of the second semipermeable membrane means.

As discussed previously, hemodiafiltration utilizes both diffusive and convective mass transfer and thus wastes are removed from the blood in the hemodiafiltration cartridge of the invention by diffusion down a concentration gradient as well as by transfer due to the differential in pressure between the blood stream and dialysate stream at different parts of the cartridge. Some blood plasma water is removed from the blood due to said pressure differential and the portion of the dialysate which enters the hollow fibers of the second semipermeable membrane means through the walls of said hollow fibers and serves to replace at least some of the blood plasma water lost from the blood enters said hollow fibers also due to said pressure differential. In the cartridge of the invention, said pressure differential is produced because the inlet pressure of the blood is greater than the outlet pressure of the dialysate and the inlet pressure of the dialysate is greater than the outlet pressure of the blood. For instance, the inlet Pressure of the blood may be 200 mmHg, the outlet pressure of the blood may be 50 mmHg, the inlet pressure of the dialysate may be 80 mmHg and the outlet pressure of the dialysate may be 30 mmHg. In the area of the cartridge where the dialysate pressure is greater than that of the blood, backfiltration occurs, i.e. dialysate enters the hollow fibers of the second semipermeable membrane means through the walls of said hollow fibers. In the area of the cartridge where the blood pressure is greater than the dialysate pressure, blood wastes and blood plasma water pass from the blood in the hollow fibers of the second semipermeable membrane means into the dialysate surrounding the second semimpermeable membrane means. By adjusting the pressure differential, the amount of sterile and non-pyrogenic dialysate which enters into the hollow fibers of the second semipermeable membrane means can be regulated. This regulation can take place, for example, by adjusting the outlet pressure of the dialysate and/or the outlet pressure of the blood. For instance, one can change the outlet pressure of blood by tightening a clamp on the tubing that goes from the blood outlet to the patient's bloodstream. Preferably, there is enough backfiltration of the sterile and non-pyrogenic dialysate to maintain the net fluid loss from the patient at less than 20 ml/min.

A standard dialysate (dialysis fluid) is used in the method of the invention. Uremic substances, such as urea and creatinine, being small molecules, will pass by diffusion through the walls of the hollow fibers of the second semipermeable membrane means to the dialysate. Standard dialysates are basically water supplemented with electrolytes and glucose. The electrolytes, e.g. $Mg^{++}$, $K^+$, $Na^+$, $Cl^-$ and $HCO_3^-$ are added to the dialysate so as to prevent excessive ion removal. $Ca^{++}$ is also generally added to the dialysate so as to cause addition of calcium to the patient's blood, as the total body calcium in kidney failure patients is often low.

While this invention has been described with reference to its preferred embodiments, other embodiments can achieve the same result. Variations and modifications of the present invention will be obvious to those skilled in the art and it is intended to cover in the appended claims all such modifications and equivalents as fall within the spirit and scope of this invention.

I claim:

1. A hemodiafiltration cartridge comprising:
 means defining a dialysate chamber;
 means defining a dialysate inlet;
 means defining a dialysate outlet;
 means defining a blood chamber;
 means defining a blood inlet;
 means defining a blood outlet;
 a first semipermeable membrane means within said dialysate chamber for sterilizing and depyrogenating dialysate prior to its contact with blood; and a second semipermeable membrane means within said blood chamber for the removal of wastes from blood.

2. The hemodiafiltration cartridge of claim 1 wherein the cartridge is generally tubular and has two ends, a first end and a second end, and where the dialysate inlet is located at or adjacent to the first end of said cartridge, the dialysate outlet is located at or adjacent to the second end of said cartridge, the blood inlet is located at or adjacent to the second end of said cartridge, and the blood outlet is located at or adjacent to the first end of said cartridge.

3. The hemodiafiltration cartridge of claim 2 wherein said second semipermeable membrane means comprises a plurality of semipermeable hollow fibers, all of said hollow fibers being open at both ends, said plurality of semipermeable hollow fibers extending generally longitudinally through said cartridge from said first end of said cartridge to said second end of said cartridge, the plurality of semipermeable hollow fibers having two ends, one end being in communication with the blood inlet and the other end being in communication with the blood outlet and said first semipermeable membrane means comprises a plurality of semipermeable hollow fibers, all of said hollow fibers being open at the same end and being closed at the opposite end, said plurality of semipermeable hollow fibers extending generally longitudinally in said cartridge from said first end of said cartridge towards the second end of said cartridge, said open ends of said hollow fibers of the first semipermeable membrane means extending to the first end of said cartridge and being in communication with the dialysate inlet in order for dialysate to be able to flow into said hollow fibers.

4. The hemodiafiltration cartridge of claim 3 wherein the plurality of semipermeable hollow fibers of said first semipermeable membrane means extend generally longitudinally in said cartridge from said first end of said cartridge towards the second end of said cartridge but do not reach the second end of said cartridge and wherein the hemodiafiltration cartridge further comprises a plenum extending generally longitudinally from said closed ends of the hollow fibers of the first semipermeable membrane means to the second end of the cartridge, said plenum being in communication with the dialysate outlet.

5. The hemodiafiltration cartridge of claim 4 wherein the first end of the cartridge is defined by a first end wall having openings for the dialysate inlet and the blood outlet; the second end of the cartridge is defined by a second end wall having openings for the dialysate outlet and the blood inlet; the cartridge has two generally cylindrical chambers, said blood chamber and said dialysate chamber, said blood chamber containing the second semipermeable membrane means and said dialysate chamber containing the first semipermeable membrane means and the plenum extending from the closed ends of the hollow fibers of the first semipermeable membrane means to the second end of the cartridge, the dialysate inlet being located on the portion of the first end wall of the cartridge which bounds the dialysate chamber, the dialysate outlet being located on the portion of the second end wall of the cartridge which bounds the dialysate chamber, the blood inlet being located on the portion of the second end wall of the cartridge which bounds the blood chamber and the blood outlet being located on the portion of the first end wall of the cartridge which bounds the blood chamber and wherein said hemodiafiltration cartridge further comprises a first separating means which separates said blood chamber and dialysate chamber at the first end of the cartridge and a second separating means which separates said blood chamber and dialysate cnamber at the second end of the cartridge.

6. The hemodiafiltration cartridge of claim 5 wherein the dialysate chamber and the blood chamber are partially separated from each other in the interior of the cartridge by a first barrier means extending substantially longitudinally in said cartridge from said closed ends of the hollow fibers of the first semipermeable membrane means towards said first end of said cartridge but not reaching the first end of said cartridge, the space from the end of the first barrier means to the first end of the cartridge serving to allow dialysate to flow from said dialysate chamber into said blood chamber.

7. The hemodiafiltration cartridge of claim 6 wherein the plenum extending from said closed ends of the hollow fibers of the first semipermeable membrane means to the second end of the cartridge is bounded by a second barrier means which extends laterally between said closed ends of the hollow fibers and said plenum.

8. The hemodiafiltration cartridge of claim 3 wherein the plurality of semipermeable hollow fibers of said first semipermeable membrane means extend generally longitudinally in said cartridge from said first end of said cartridge to said second end of said cartridge.

9. The hemodiafiltration cartridge of claim 2 wherein said second semipermeable membrane means comprises a plurality of semipermeable hollow fibers, all of said hollow fibers being open at both ends, said plurality of semipermeable hollow fibers extending generally longitudinally through said cartridge from said first end of said cartridge to said second end of said cartridge, said plurality of semipermeable hollow fibers having two ends, one end being in communication with the blood inlet and the other end being in communication with the blood outlet and said first semipermeable membrane means comprises a plurality of semipermeable hollow fibers, all of said hollow fibers being open at both ends, said plurality of semipermeable hollow fibers extending generally longitudinally in said cartridge from said first end of said cartridge towards the second end of said cartridge, said plurality of hollow fibers of the first semipermeable membrane means having two ends, a first bundle end and a second bundle end, the first bundle end extending to the first end of said cartridge and being in communication with the dialysate inlet in order for dialysate to be able to flow into said hollow fibers, said second bundle end being in communication with the outside of the cartridge via a tiny opening.

10. The hemodiafiltration cartridge of claim 9 wherein the plurality of semipermeable hollow fibers of said first semipermeable membrane means extend generally longitudinally in said cartridge from said first end of said cartridge towards the second end of said cartridge but do not reach the second end of said cartridge and wherein the hemodiafiltration cartridge further comprises a plenum extending generally longitudinally from said second bundle end of the hollow fibers of the first semipermeable membrane means to the second end of the cartridge, said plenum being in communication with the dialysate outlet and said plenum being bounded by a second barrier means which extends laterally between said second bundle end and said plenum, said tiny opening through which the second bundle end is in communication with the outside of the cartridge being located in said second barrier means so that air and a minimal amount of dialysate can pass from the hollow fibers of the first semipermeable membrane means into said plenum via said tiny opening in the second barrier means and then out of said cartridge via said dialysate outlet.

11. The hemodiafiltration cartridge of claim 10 wherein the first end of the cartridge is defined by a first end wall having openings for the dialysate inlet and the blood outlet; the second end of the cartridge is defined by a second end wall having openings for the dialysate outlet and the blood inlet; the cartridge has two generally cylindrical chambers, said blood chamber and said dialysate chamber, said blood chamber containing the second semipermeable membrane means and said dialysate chamber containing the first semipermeable membrane means and the plenum extending from the second bundle end of the hollow fibers of the first semipermeable membrane means to the second end of the cartridge, the dialysate inlet being located on the portion of the first end wall of the cartridge which bounds the dialysate chamber, the dialysate outlet being located on the portion of the second end wall of the cartridge which bounds the dialysate chamber, the blood inlet being located on the portion of the second end wall of the cartridge which bounds the blood chamber and the blood outlet being located on the portion of the first end wall of the cartridge which bounds the blood chamber and wherein said hemodiafiltration cartridge further comprises a first separating means which separates said blood chamber and dialysate chamber at the first end of the cartridge and a second separating means which separates said blood chamber and dialysate chamber at the second end of the cartridge.

12. The hemodiafiltration cartridge of claim 11 wherein both the first and second separatng means comprise an O-ring.

13. The hemodiafiltration cartridge of claim 11 wherein the dialysate chamber and the blood chamber are partially separated from each other in the interior of the cartridge by a first barrier means extending substantially longitudinally in said cartridge from said second bundle end of the hollow fibers of the first semipermeable membrane means towards said first end of said cartridge but not reaching the first end of said cartridge, the space from the end of the first barrier means to the first end of the cartridge serving to allow dialysate to flow from said dialysate chamber into said blood chamber.

14. The hemodiafiltration cartridge of claim 9 wherein the plurality of semipermeable hollow fibers of said first semipermeable membrane means and the plurality of semipermeable hollow fibers of said second semipermeable membrane means can be made from the same material or a different material, said material being selected from the group consisting of polysulfone, polyamide, polyacrylonitrile and cellulose acetate.

15. The hemodiafiltration cartridge of claim 9 wherein the semipermeable hollow fibers of said first semipermeable membrane means have molecular weight pore size cutoffs of at least 1000 daltons.

16. The hemodiafiltration cartridge of claim 9 wherein the semipermeable hollow fibers of said second semipermeable membrane means have molecular weight pore size cutoffs of up to 55,000 daltons.

17. The hemodiafiltration cartridge of claim 9 wherein the packing density of the semipermeable hollow fibers of said first semipermeable membrane means is between about 30% and about 70%.

18. The hemodiafiltration cartridge of claim 9 wherein the packing density of the semipermeable hollow fibers of said second semipermeable membrane means is between about 30% and about 70%.

19. A hemodiafiltration apparatus comprising;
the hemodiafiltration cartridge of claim 2;
a dialysate reservoir;
first conduit means connecting said dialysate reservoir to said dialysate inlet of said cartridge;
first conveying means for passing dialysate from said dialysate r--servoir through the first conduit means into said cartridge via said dialysate inlet and out of said cartridge via said dialysate outlet;
second conduit means connecting a blood stream to said blood inlet of said cartridge;
third conduit means connecting said blood outlet of said cartridge to said blood stream; and
second conveying means for passing blood from said blood stream through the second conduit means into said cartridge via said blood inlet and for passing treated blood out of said cartridge to said blood stream via said blood outlet and via said third conduit means connecting said blood outlet to said blood stream.

20. A hemodiafiltration apparatus comprising;
the hemodiafiltration cartridge of claim 7;
a dialysate reservoir;
first conduit means connecting said dialysate reservoir to said dialysate inlet of said cartridge;
first conveying means for passing dialysate from said dialysate reservoir through the first conduit means into said cartridge via said dialysate inlet and out of said cartridge via said dialysate outlet;
second conduit means connecting a blood stream to said blood inlet of said cartridge;
third conduit means connecting said blood outlet of said cartridge to said blood stream; and
second conveying means for passing blood from said blood stream through the second conduit means into said cartridge via said blood inlet and for passing treated blood out of said car ridge to said blood stream via said blood outlet and via said third conduit means connecting said blood outlet to said blood stream.

21. A hemodiafiltration apparatus comprising:
the hemodiafiltration cartridge of claim 13;
a dialysate reservoir;
first conduit means connecting said dialysate reservoir to said dialysate inlet of said cartridge;
first conveying means for passing dialysate from said dialysate reservoir through the first conduit means into said cartridge via said dialysate inlet and out of said cartridge via said dialysate outlet;
second conduit means connecting a blood stream to said blood inlet of said cartridge;
third conduit means connecting said blood outlet of said cartridge to said blood stream; and
second conveying means for passing blood from said blood stream through the second conduit means into said cartridge via said blood inlet and for passing treated blood out of said cartridge to said blood stream via said blood outlet and via said third conduit means connecting said blood outlet to said blood stream.

22. A hemodiafiltration method comprising the steps of:
(a) providing the hemodiafiltration cartridge of claim 3;
(b) passing dialysate through the dialysate inlet into said hollow fibers of the first semipermeabe membrane means and through the walls of the hollow fibers of the first semipermeable membrane means, a portion of said dialysate entering into the hollow fibers of the second semipermeable membrane means through the walls of the hollow fibers of the second semipermeable membrane means and the remainder of the dialysate surrounding the exterior of the hollow fibers of the second semipermeable membrane means;
passing blood through the blood inlet and into said hollow fibers of the second semipermeable membrane means;
(d) passing blood wastes and blood plasma water through the walls of the hollow fibers of the second semipermeable membrane means into said dialysate surrounding the second semipermeable membrane means;
(e) pa sing the blood minus the blood wastes and blood plasma water in the hollow fibers of the second semipermeable membrane means together with the dialysate in the hollow fibers of the second semipermeable membrane means into the blood outlet; and
(f) passing dialysate surrounding the second semipermeable membrane means with the blood wastes and blood plasma water lost from the blood into the dialysate outlet.

23. The method of claim 22 wherein the flow direction of the blood in the hollow fibers of the second semipermeable membrane means from .ntroducution to withdrawal is substantially opposit to the flow direction of the dialysate which has passed through the walls of the hollow fibers of the first semipermeable membrane means.

24. A hemodiafiltration method comprising the steps of:
(a) providing the hemodiafiltration cartridge of claim 7;
(b) Passing dialysate through the dialysate inlet into said hollow fibers of the first semipermeable membrane means and through the walls of the hollow fibers of the first semipermeable membrane means into said blood chamber at the space from the end of the first barrier means to the first end of the carrridge, a portion of said dialysate entering into the hollow fibers of the second semipermeable membrane means through the walls of the hollow fibers of the second semipermeable membrane means and the reminder of the dialysate surrounding the exterior of the hollow fibers of the second semipermeable membrane means and flowing from the first end of the cartridge to the second end of the cartridge;
(c) passing blood through the blood inlet and into said hollow fibers of the second semipermeable membrane means;
(d) passing blood wastes and blood plasma water through the walls of the hollow fibers of the second semipermeable membrane means into said dialysate surrounding the second semipermeable membrane means;
(e) passing the blood minus the blood wastes and blood plasma water in the hollow fibers of the second semipermeable membrane means together with the dialysate in the hollow fibers of the second semipermeable membrane means into the blood outlet; and (f) passing dialysate surrounding the second semipermeable membrane means with the blood washes and blood plasma water lost from the blood into the dialysate outlet via the plenum extending from the closed ends of the hollow fibers of the first semipermeable membrane means to the second end of the cartridge.

25. The method of claim 24 wherein the inlet pressure of the blood is greater than the outlet pressure of the dialysate and the inlet pressure of the dialysate is greater than the outlet pressure of the blood.

26. The method of claim 24 wherein the flow direction of the blood in the hollow fibers of the second semipermeable membrane means from introduction to withdrawal is substantially opposite to the flow direction of the dialysate in the blood chamber.

27. A hemodiafiltration method comprising the steps of:

(a) providing the hemodiafiltration cartridge of claim 9:

(b) passing dialysate through the dialysate inlet into said hollow fibers of the first semipermeable membrane means;

(c) passing dialysate from the hollow fibers of the first semipermeable membrane means through the walls of the hollow fibers of the first semipermeable membrane means, a portion of said dialysate entering into the hollow fibers of the second semipermeable membrane means through the walls of the hollow fibers of the second semipermeable membrane means and the remainder of the dialysate surrounding the exterior of the hollow fibers of the second semipermeable membrane means;

(d) passing blood through the blood inlet and into said hollow fibers of the second semipermeable membrane means;

(e) passing blood wastes and blood plasma water through the walls of the hollow fibers of the second semipermeable membrane means into said dialysate surrounding the second semipermeable membrane means;

(f) passing the blood minus the blood wastes and blood plasma water in the hollow fibers of the second semipermeable membrane means together with the dialysate in the hollow fibers of the second semipermeable membrane means into the blood outlet; and (g) passing dialysate surrounding the second semipermeable membrane means with the blood wastes and blood plasma water lost from the blood into the dialysate outlet.

28. The merhod of claim 27 further comprising the step of passing air in the hollow fibers of the first semipermeable membrane means out of said cartridge via said tiny opening.

29. The met od of claim 28 wherein a minimal amount of dialysate in the h.llow fibers of the first semipermeable membrane passes with said air out of said cartridge via said tiny opening, the remainder of the dialysate which has entered into said hollow fibers of the first semipermeable membrane means through the dialysate inlet being passed through the walls of the hollow fibers of the first semipermeable membrane means in step (c).

30. The method of claim 28 wherein the inlet pressure of the blood is greater than the outlet pressure of the dialysate and the inlet pressure of the dialysate is greater than the outlet pressure of the blood.

31. The method of claim 28 wherein the dialysate passed into the dialylate inlet in step (b) is unsterile and the dialysate which has passed through the walls of the hollow fibers of the first semipermeable membrane means and into the hollow fibers of the second semipermeable membrane means through the walls of rhe hollow fibers of the second semipermeable membrane means in step (c) is sterile and non-pyrogenic.

32. The method of claim 28 wherein the flow direction of the blood in the hollow fibers of the second semipermeable membrane means from introduction to withdrawal is substantially opposite to the flow direction of the dialysate which has passed through the walls of the hollow fibers of the first semipermeable membrane means.

33. A hemodiafiltration method comprising the steps of:

(a) providing the hemodiafiltration cartridge of claim 13;

(b) passinq dialysate throuqh the dialysate inlet into said hollow fibers of the first sempermeable membrane means;

(c) passing dialysate from the hollow fibers of the first semipermeable membrane means through the walls of the hollow fibers of the first semipermeable membrane means into said blood chamber at the space from the end of the first barrier means to the first end of the cartridge, a portion of said dialysate entering into the hollow fibers of the second semipermeable membrane means through the walls of the hollow fibers of the second semipermeable membrane means and the remainder of the dialysate surrounding the exterior of the hollow fibers of the second semipermeable membrane means and flowing from the first end of the cartridge to the second end of the cartridge; (d) passing blood through the blood inlet and into said hollow fibers of the second semipermeable membrane means;

(e) passing blood wastes and blood plasma water through the walls of the hollow fibers of the second semipermeable membrane means into said dialysate surrounding the second semipermeable membrane means;

(f) passing the blood minus the blood wastes and blood plasma water in the hollow fibers of the second semipermeable membrane means together with the dialysate in the hollow fibers of the second semipermeable membrane means into the blood outlet; and (g) passing dialysate surrounding the second semipermeable membrane means with the blood wastes and blood plasma water lost from the blood into the dialysate outlet via the plenum extending from the second bundle end of the hollow fibers of the first semipermeable membrane means to the second end of the cartridge.

34. The method of claim 33 further comprising the step of passing air in the hollow fibers of the first semipermeable membrane means into said plenum via said tiny opening in the second barrier means and then out of said cartridge via said dialysate outlet.

35. The method of claim 34 wherein a minimal amount of dialysate in the hollow fibers of the first semipermeable membrane means passes with said air into said plenum via said tiny opening in the second barrier means and then out of said cartridge via the dialysate outlet, the remainder of the dialysate which has entered into said hollow fibers of the first semipermeable membrane means through the dialysate inlet being passed through the walls of the hollow fibers of the first semipermeable membrane means in step (c).

36. The method of claim 35 wherein the minimal amount of dialysate comprises less than 10 percent of the dialysate which has entered into the hollow fibers of the first semipermeable membrane means via the dialysate inlet.

37. The method of claim 36 wherein the minimal amount of dialysate comprises less than 5 percent of the dialysate which has entered into the hollow fibers of the first semipermeable membrane means via the dialysate inlet.

38. The method of claim 34 wherein the inlet pressure of the blood is greater than the outlet pressure of the dialysate and the inlet pressure of the dialysate is greater than the outlet pressure of the blood.

39. The method of claim 34 wherein the flow direction of the blood in the hollow fibers of the second semipermeable membrane means from introduction to withdrawal is substantially opposite to the flow direction of the dialysate in the blood chamber.

40. The method of claim 34 wherein the dialysate passed into the dialysate inlet in step (b) is unsterile and the dialysate which has passed through the walls of the hollow fibers of the first semipermeable membrane means and into the hollow fibers of the second semipermeable membrane means through the walls of the hollow fibers of the second semipermeable membrane means in step (c) is sterile and non-pyrogenic.

41. The method of claim 40 wherein the amount of dialysate entering into the hollow fibers of the second semipermeable membrane means through the walls of the hollow fibers of the second semipermeable membrane means is regulated.

42. The method of claim 41 wherein said regulation of the amount of dialysate occurs by adjusting the outlet pressure of the dialysate or the outlet pressure of the blood or both.

* * * * *